United States Patent [19]

Schubart et al.

[11] Patent Number: 4,534,901
[45] Date of Patent: Aug. 13, 1985

[54] COBALT-BORON COMPOUNDS

[75] Inventors: Rüdiger Schubart; Hans Magg, both of Bergisch-Gladbach, Fed. Rep. of Germany

[73] Assignee: Bayer Aktiengesellschaft, Leverkusen, Fed. Rep. of Germany

[21] Appl. No.: 523,968

[22] Filed: Aug. 17, 1983

[30] Foreign Application Priority Data

Aug. 27, 1982 [DE] Fed. Rep. of Germany ....... 3231913

[51] Int. Cl.³ ............................................. C07F 15/06
[52] U.S. Cl. ......................................... 556/7; 524/328
[58] Field of Search .................................... 260/439 R

[56] References Cited

U.S. PATENT DOCUMENTS 3,438,799  4/1969  Eck et al. .............................. 427/327
4,360,473  11/1982  Marzocchi et al. ......... 260/439 R X
4,416,824  11/1983  Reimer et al. .................... 260/439 R

OTHER PUBLICATIONS

Chemical Abstracts 68, 56059x, (1968).

Primary Examiner—Helen M. S. Sneed
Attorney, Agent, or Firm—Connolly and Hutz

[57] ABSTRACT

Compounds corresponding to the formula

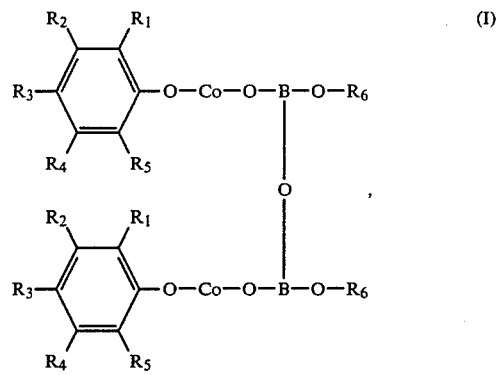

wherein $R_1$, $R_2$, $R_3$, $R_4$ and $R_5$ are the same or different, and represent hydrogen, hydroxy, $C_1$-$C_{18}$ alkyl, $C_5$-$C_{12}$ cycloalkyl, $C_1$-$C_{16}$ alkylthio, $C_6$-$C_{14}$ aryl, $C_6$-$C_{14}$ aryl-$C_1$-$C_4$ alkyl, $C_1$-$C_{18}$ alkoxy, $C_6$-$C_{14}$ aryloxy, $C_6$-$C_{14}$-aryl-$C_1$-$C_4$ alkyloxy, halogen or a hydrocarbon radical which has from 1 to 18 carbon atoms and has one or more double bonds, and $R_6$ represents a linear or branched, saturated or mono- or poly-unsaturated hydrocarbon radical having from 1 to 22 carbon atoms or a radical of the formula

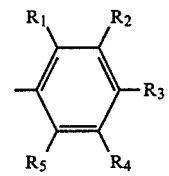

wherein $R_1$ to $R_5$ have the above-mentioned meaning.

2 Claims, No Drawings

COBALT-BORON COMPOUNDS

Many commercial rubber articles, for example pneumatic tyres, conveyor belts or high-pressure hoses, are provided with reinforcing inserts of steel which has a high carbon content and is often used in the form of steel cords.

A strong and lasting bond between metal and rubber is necessary in order to ensure a good efficiency and life of the articles.

In the absence of additional adhesive, this can only be achieved if the filaments of the steel cord are plated with a thin layer of α-brass or with another alloy having the main constituents copper and zinc or with pure zinc.

The cord thus treated is directly vulcanised into the rubber mixture which usually contains in particular adhesion-promoting additives.

The most common additives for improving the binding power, hereinafter termed "adhesives" may be classified into two groups according to their chemical structure.

The first group includes all adhesives which are only efficient as multicomponent systems.

It is common to them all that they contain highly active silicas.

The other components are resorcinol or resorcinol-formaldehyde condensation products and formaldehyde-releasing compounds, such as hexamethylene tetramine, etherified or esterified methylolmalamines having different degrees of etherification or esterification, and condensation products thereof.

Although these systems produce good adhesion values, they sometimes give rise to vapours and an unpleasant odour during vulcanisation. Furthermore, the processibility in the mixing machines, for example on a roller mixer, is severely impaired because resorcinol tends towards sublimation, particularly at a temperature in the vicinity of its melting point.

Organometallic compounds belong to the second group, and the compounds of cobalt predominate. Above all, cobalt soaps, of the type which are also conventional as siccatives in the lacquer industry, have been used for a comparatively long time.

Thus, FR-PS, No. 1,323,934 claims various cobalt salts, for example cobalt stearate, cobalt linolate or cobalt naphthenate. Boron-organic cobalt compounds, corresponding to U.S. Pat. No. 3,296,242, are also suitable. In addition to cobalt, the following are also included as metals: copper, nickel, lead or zinc. (See DE-OS No. 2,303,674; DE-OS No. 2,447,853 or U.S. Pat. No. 4,154,911).

Other compound classes include nickel and cobalt complexes of succinylosuccinic acid esters (EP-OS No. 0,003,820) or transition metal salts of some 1,2-diols (EP-OS No. 0,009,000).

Single organic salts do not generally improve the adhesion of a rubber mass to metallic carrier materials. On the contrary, they often act as rubber poisons and reduce the stability of the rubber-metal bond.

There are clear differences in effect between the adhesives of the first group and those of the second group.

Organometallic compounds, added to the rubber mixture, usually result in an improved metal-rubber adhesion after vulcanisation, and may also retard, in a lasting manner, the corrosion of the metallic carrier.

However, they have a substantial disadvantage in that the adhesiveness is greatly reduced, in particular in the case of high temperature vulcanisation (180°–240° C.). The reversion also becomes noticeable in a very disadvantageous manner.

However, the adhesives of the first group have a better resistance of the rubber-metal bond to reheating procedures. Such bonds with the adhesives of the second group are also more sensitive to heat and moisture influences.

Thus, adhesive combinations are also frequently added to the adhesive mixtures, in which case either individual components of an adhesive system, or the adhesive system as a whole may be used (DE-OS No. 1,720,144; DE-OS No. 2,841,401).

A disadvantage of all adhesive systems which correspond to the prior art is the sensitivity of the rubber-metal bond, which is promoted or caused by such systems, to the influence of moisture or of moisture together with heat.

Therefore, there is interest in an adhesive system which has the greatest possible resistance to such influences.

Thus, an object of the present invention is to provide an adhesive system for rubber-metal adhesion which does not have the above-mentioned disadvantages or does not have such disadvantages to the previous extent.

New cobalt compounds have now been found which are outstandingly suitable for such adhesive systems.

Therefore, the present invention provides compounds corresponding to the formula:

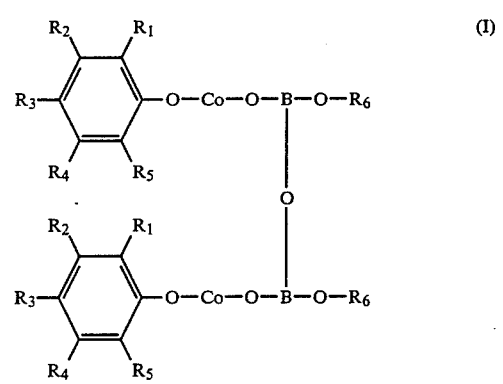

wherein $R_1$, $R_2$, $R_3$, $R_4$ and $R_5$ are the same or different, and represent hydrogen, hydroxy, $C_1$–$C_{18}$ alkyl, $C_5$–$C_{12}$ cycloalkyl, $C_1$–$C_{16}$ alkylthio, $C_6$–$C_{14}$ aryl, $C_6$–$C_{14}$ aryl-$C_1$–$C_4$ alkyl, $C_1$–$C_{18}$ alkoxy, $C_6$–$C_{14}$ aryloxy, $C_6$–$C_{14}$-aryl-$C_1$–$C_4$ alkyloxy, halogen or a hydrocarbon radical having from 2 to 18 carbon atoms and having one or more double bonds, and $R_6$ represents a linear or branched, saturated or mono- or poly-unsaturated hydrocarbon radical having from 1 to 22 carbon atoms, or a radical of the formula

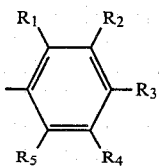

wherein $R_1$, $R_2$, $R_3$, $R_4$ and $R_5$ have the above mentioned meaning.

Preferred compounds contain one radical of the formula

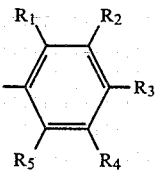

per boron atom.

The compounds corresponding to formula I are obtained by reacting, while heating
(a) a cobalt salt of a $C_1$–$C_4$ carboxylic acid,
(b) an optionally substituted phenol,
(c) a boric acid trialkylester and
(d) optionally a linear or branched, saturated or mono- or poly-unsaturated $C_8$–$C_{22}$ alcohol.

Preferably the compounds are reacted in such amounts that per mol of cobalt salt one mol boric acid trialkyl ester, one to two mols phenol and zero to one mol $C_8$–$C_{22}$-alcohol are added, wherein the sum of components (b) and (d) is at most 2 mols.

The boric acid trialkylester can be added in substance or can be produced in situ from boron trioxide and a $C_1$–$C_7$-alcohol, which can be added in excess. Excess $C_1$–$C_7$-alcohol and alcohol which is released from boric acid trialkyl ester is distilled off.

The present invention also relates to a process for increasing the adhesivenss between rubber and metals, characterised in that a compound corresponding to formula I is added to the rubber.

The following are mentioned as preferred carboxylic acid components of the cobalt salt: acetic acid, formic acid, propionic acid or butyric acid, in particular acetic acid.

The radicals $R_1$, $R_2$, $R_4$ and $R_5$ preferably represent hydrogen, and $R_3$ preferably represents $C_6$–$C_{12}$ alkyl or $C_6$–$C_{14}$ aryl-$C_1$–$C_4$ alkyl.

The compounds may be present as an isomeric mixture.

In particular, the radicals $R_1$ to $R_5$ may represent the following: hydrogen, methyl, ethyl, propyl, iso-propyl, n-butyl, sec. butyl, iso-butyl, tert.-butyl, n-pentyl, iso-pentyl, sec.-pentyl, neopentyl, n-hexyl, iso-hexyl, sec.-hexyl, cyclohexyl, n, heptyl, iso-heptyl, tert.-heptyl, octyl, 2-ethylhexyl, nonyl, decyl, undecyl, dodecyl, tridecyl, tetradecyl, pentadecyl, hexadecyl, heptadecyl, octadecyl, methyl-cyclohexyl, cyclohexylmethyl, naphthyl, anthracenyl, naphthylmethyl, cycloheptyl, cyclooctyl, phenyl, benzyl, cyclononyl, cyclodecyl, cycloundecyl, cyclododecyl, 9-octadecenyl or methylphenyl.

The same radicals as those mentioned under alkyl, but merely extended with oxygen or sulphur, may be mentioned as alkoxy and alkylthio.

However, pure or isomeric compounds of butylphenol, propylphenol, octylphenol, nonylphenol benzylphenol, dodecylphenol and tolylcresol are generally used. Nonylphenol, dodecylphenol, tolylcresol and benzylphenol are preferred.

The following compounds are mentioned as $C_8$–$C_{22}$ alcohols: n-octanol, 2-ethylhexanol, n-nonanol, trimethylhexanol (commercial isomer mixture), decanol, undecanol, dodecanol, tridecanol, tetradecanol, pentadecanol, hexadecanol, heptadecanol, octadecanol, octadecenyl alcohol, nonadecanol or $C_{20}$–$C_{22}$ alcohols, olein alcohol and mixtures of saturated or mono- or poly-unsaturated $C_{10}$–$C_{22}$ alcohols, in particular natural and commercial mixtures.

Esters having in each case $C_1$–$C_8$, preferably $C_3$–$C_5$, and in particular $C_4$ alkyl, for example isobutyl, groups are mentioned as boric acid trialkylesters.

The adhesive system produces good adhesion values, clearly improves the ageing values of the rubber articles (for example steam ageing) and reduces the reversion.

The adhesive system is added to the rubber within the quantity range which is conventional for these systems. The quantities are generally from 0.1 to 20% by weight, preferably from 0.2 to 10% by weight, and in particular from 0.3 to 5% by weight, based on the rubber.

The production of the compounds corresponding to formula I is a three-to-five-component reaction. The following combinations of starting materials are preferred, cobalt acetate-tetrahydrate being used in every case as the cobalt salt.

| No. | Boron compound | Phenol | Alcohol |
| --- | --- | --- | --- |
| 1 | Tributylester | Nonylphenol | — |
| 2 | Tri-2-ethylhexylester | Nonylphenol | — |
| 3 | Tri-(trimethylhexyl)ester | Nonylphenol | — |
| 4 | Tributylester | isom.-p-tolyl phenol | — |
| 5 | Tri-(trimethylhexyl)ester | isom.-p-tolylphenol | — |
| 6 | Tri-2-ethylhexylester | isom.-p-tolylphenol | — |
| 7 | Tri-isobutylester | isom.-p-tolylphenol | — |
| 8 | Tri-isobutylester | Nonylphenol | Tetradecanol |
| 9 | Trioxide/Isobutanol | Nonylphenol | Tetradecanol |
| 10 | Tri-isobutylester | Nonylphenol | Stearyl alcohol |
| 11 | Tri-isobutylester | Nonylphenol | $C_{14}$–$C_{22}$ fatty alcohol mixture |
| 12 | Tri-isobutylester | Nonylphenol | 9-octadecenyl alcohol* |
| 13 | Tri-isobutylester | Nonylphenol | $C_{12}$–$C_{18}$ fatty alcohol mixture |
| 14 | Tri-isobutylester | isom.-p-tolylphenol | Dodecanol |
| 15 | Tri-isobutylester | Nonylphenol | Dodecanol |
| 16 | Tri-isobutylester | Dodecylphenol | Dodecanol |

*90% of 9-octadecenyl alcohol and various $C_8$–$C_{22}$ alcohols.
2,3,8,9,10,11,12,13,15 and 16 are particularly preferred products.

The process is explained using the following Example.

249 g of cobalt acetate-tetrahydrate are mixed with 220 g of nonylphenol (commercial isomer mixture) and heated with stirring under normal pressure up to 200° C. in an apparatus provided with a column. The water of crystallisation is split off during this operation. The mixture is then cooled to 140° to 160° C. and stirred under vacuum for several hours to remove residues of moisture.

A mixture of 230 g of boric acid triisobutyl ester and 214 g of tetradecanol is then added (may be added at 140° C.) and the mixture is further heated slowly. After a short initial foaming, a volatile reaction product distills off at from 90° to 115° C. The internal temperature is slowly increased as the distillation of the volatile product of isobutanol and isobutyl acetate subsides. At an internal temperature of from 220° to 240° C., the distillation of the volatile mixture is completed after some time. The mixture is then stirred for 2 to 3 hours, cooled to 200° C. and evacuated. 560 g of a dark blue, low viscosity oil is obtained having the following elemental analytical composition:

| | | |
|---|---|---|
| C | found | 64.7% |
| H | | 9.9 |
| B | | 2.1 |
| Co | | 11.0 |

The dehydration of the cobalt salt which is described above may also be carried out by azeotropic distillation using toluene or xylene.

In a variant, boric acid trioxide and excess isobutanol are used instead of boric acid trialkylester.

An additional increase in the adhesiveness may be achieved by adding to the rubber, in addition to the compound corresponding to formula I, a formaldehyde-releasing compound in quantities of from 0.01 to 10% by weight, preferably from 1 to 3% by weight, based on the rubber.

Moreover, the following may also be added to the rubber in quantities of from 0.01 to 10% by weight, preferably from 0.5 to 5% by weight, based on the rubber: resorcinol or derivatives thereof, such as dimethoxybenzene, diacetoxybenzene, dibenzoyloxybenzene, dipropoxybenzene, dipropionyloxybenzene, di(-trimethylsilyloxy)benzene, and sulphoesters, phosphoric acid esters, phosphorous acid esters and urethanes and carbonates of resorcinol.

The resorcinol compound may be added to the rubber separately or combined with the formaldehyde-releasing compound. It is also possible to add resorcinol precondensed with formaldehyde in quantities of from 0.01 to 10% by weight, preferably from 3 to 5% by weight, based on rubber, the precondensate containing from 1 to 3 mols of formaldehyde per mole of resorcinol.

Furthermore, silica may be added in the conventional quantities.

The expression "formaldehyde-releasing compounds" is understood as designating those substances which, upon heating, for example at a temperature ranging from 40° to 200° C., in particular under vulcanisation conditions, are capable of splitting off formaldehyde, optionally in the presence of water. When methylol esters are used, condensation reactions may also occur with the release of alcohols or acids. These products will be termed hereinafter in brief "formaldehyde-releasers".

They are known and described in BL-PS No. 621 923, 624 519, U.S. Pat. No. 2,512,128 "Helvetica chimica acta", 24, P. 315 E, CH-PS No. 197 486 and Houben-Weyl, "Methoden der organischen Chemie volume 8, P. 242.

Particularly high adhesions are obtained using the following: hexamethylol melamine, hexamethylol melamine-pentamethylether, mixtures of hexamethylol melamine-tetramethylether and -trimethylether, pentamethylol melamine-trimethylether, tetramethylolhydrazodicarbonamide, tetramethylol-acetylene-diurea, N,N'-dimethylol-urea, N-methylol-dicyanodiamide, methylene-amino-acetonitrile, N-allyl-dioxazine, N-phenyl-dioxazine, 1-aza-3,7-di-oxabicyclo[3,3]-octane, and hexamethylene tetramine.

The rubber masses provided with the above-mentioned adhesive combination result in outstanding adhesion properties with respect to iron, copper, brass, zinc, bronze, aluminium and other reinforcing metals. Typical types of rubber which may be used for such adhesive mixtures include rubbers of the diene type, such as natural rubber, polyisoprene, polybutadiene, styrene-butadiene copolymers, acrylonitrile-butadiene rubber, chloroprene rubber, EPDM and mixtures of these types mentioned above.

The rubber mixtures may contain conventional constituents, including reinforcing carbon blacks, inactive and active fillers, for example silicas and zinc oxide, processing auxiliaries, sulphur and vulcanisation accelerators.

Particularly suitable as accelerators are sulpheneamides which are derived from 2-mercaptobenzothiazole, for example N-cyclohexyl-thiobenzothiazole, N-morpholino-thiobenzothiazole, N,N-dicyclohexyl-thiobenzothiazole or N,N-diisopropylaminothiobenzothiazole. Of course, other accelerators may also be used on their own or combined together. Examples include thiurams, mercaptobenzothiazole or dithiocarbamates.

The vulcanisation temperature is selected in a manner complying with practice, for example from 120° to 220° C., preferably from 140° to 180° C.

The advantages of the present invention in the production of highly resistant bonds with steel cables or steel cords having a brass-plated surface, as they may be used, for example, in the production of rubber tyres, high-pressure hoses or conveyor belts, are illustrated by the following Examples.

These examples are based on the following mixture composition:

| | |
|---|---|
| Natural rubber (RSS 1) | 100 parts by weight |
| Carbon black N 326 | 43 " |
| Carbon black N 539 | 20 " |
| Colophonium | 3 " |
| Phenyl-β-naphthylamine | 1.5 " |
| Zinc oxide | 10 " |
| Sulphur | 7 " |
| N,N—dicyclohexyl-thiobenzothiazole | 0.7 " |

The basic mixture which is free of sulphur and accelerator is pre-mixed at 70° C. in a laboratory internal mixer and is then mixed with sulphur, accelerator and optionally adhesive in a laboratory mixing apparatus at a roller temperature of 60° C.

To test the adhesion according to the T test method (see Bayer-Mitteilungen für die Gummi-Industrie, No. 29 of 1961, P 69), test bodies are produced having dimensions of 20×15×6 mm.

Steel cords having a brass-plated surface and dimensions of 7×3×0.15 mm are used.

The test bodies are vulcanised at 150° C. corresponding to the $t_{90}$ value. For the ageing procedure, the test bodies are exposed for several days to hot air at 100° C., exposed to superheated steam at 120° C. for a few hours or are stored for several months at 40° C. and at 95% relative humidity.

If necessary, the rubber mixture is vulcanised at 180° C. for 45 minutes beyond the vulcanisation optimum.

The adhesion values are determined at 80° C. test temperature using a tension-testing device with a clamp draw-off speed of 100 mm/min. The values are stated in N/20 mm as the maximum force necessary for tearing the cord out of the rubber sample. For one measurement, at least four test bodies having the same structure are used, and the median (x) according to DIN 53, 598, and the difference between the highest and the lowest individual value, the span (R), as a measurement of the variation, are evaluated from these individual values.

Moreover, the covering of the reinforcement with rubber (C) is assessed visually after the separating test has been carried out.

The observation result is recorded in Roman numerals or in letters which satisfy the following assignment:
I: Reinforcement without any rubber covering
II: Reinforcement slightly covered with rubber
III: Reinforcement mainly covered with rubber
IV: Structural break in the rubber
GR: Complete transposition of the brass layer, bright steel on the surface.

Table 1 shows the adhesion-improving influence of some of the compounds according to the present invention.

The corresponding values with cabalt-naphthenate as an adhesion-improving substance are reproduced under "Comparison".

The numerical values show that when a compound according to the present invention is used on brass-plated steel cords, improvements in adhesion are achieved which attain the prior art level and, in some cases, surpass this level.

As is known, during the vulcanisation of sulphur-containing rubber mixtures together with reinforcements having a brass-plated surface, an adhesion-promoting layer is formed by the reaction of the copper with sulphur (see S. Buchan, Rubber to Metal Bonding, Palmerton Publishing Company New York, (1959)), which layer is particularly sensitive to influences of moisture and heat (see W. J. van OOij Rub. Chem. Techn. 51, 52 (1978)).

Table 2 demonstrates that the use of the compounds according to the present invention retards in a lasting manner the destruction of the adhesive layer which is caused by moisture and heat.

It has been found with respect to this stabilizing effect that the compounds of the present invention provide a significant advantage over the prior art.

TABLE 2

| | Co Content[+] | Test mixture vulcanised acc. to the $t_{90}$ value | | | Test mixture vulcanised acc. to the $t_{90}$ value and aged in super heated steam (2d/120° C.) | | | |
|---|---|---|---|---|---|---|---|---|
| | | X (N/20 mm) | R (N/20 mm) | C | X (N/20 mm) | R (N/20 mm) | C | X rel. (%)[++] |
| Compound No. | | | | | | | | |
| — | — | 340 | 60 | III | 100 | 10 | GR | 71 |
| 2 | 0.3 | 380 | 40 | III | 320 | 30 | II | 16 |
| 4 | 0.3 | 400 | 40 | IV | 310 | 70 | II | 22.5 |
| 8 | 0.3 | 400 | 55 | IV | 330 | 40 | II | 17.5 |
| 11 | 0.3 | 370 | 60 | IV | 285 | 80 | II | 23 |
| 16 | 0.3 | 380 | 40 | IV | 290 | 50 | III | 24 |
| 12 | 0.3 | 370 | 70 | IV | 260 | 70 | III | 29 |
| Comparison Cobalt-naphthenate | 0.3 | 380 | 90 | IV | 160 | 20 | II | 57 |

[+] in % by weight of cobalt metal, based on polymer

[++] $X \text{ rel.} = \dfrac{X \text{ (vulcanised } - t_{90} \text{ value}) - X \text{ (aged in superheated steam)}}{X \text{ (vulcanised } - t_{90} \text{ value})} \cdot 100$ Moreover, the adhesives of the previously mentioned type are distinguished by an altogether well-balanced property spectrum.

Table 3 shows, using three Compoud Examples, that the bond remains effectively adhesive even when subjected to the most varied stresses, such as thermal re-heating and the influence of moisture at true-to-practice temperatures.

TABLE 1

| | CO content[+] | Test mixture containing adhesive acc. to the present invention | | | Relevant test mixture without adhesive | | | Adhesion improvement |
|---|---|---|---|---|---|---|---|---|
| | | X (N/20 mm) | R (N/20 mm) | C | X (N/20 mm) | R (N/20 mm) | C | X (N/20 mm) |
| Compound No. | | | | | | | | |
| 1 | 0.3 | 460 | 50 | IV | 400 | 115 | III | 60 |
| 1 | 0.1 | 390 | 75 | IV | 335 | 50 | III | 55 |
| 2 | 0.3 | 485 | 50 | IV | 400 | 115 | III | 85 |
| 2 | 0.1 | 380 | 40 | III | 335 | 50 | III | 55 |
| 4 | 0.3 | 400 | 40 | IV | 340 | 60 | III | 60 |
| 8 | 0.1 | 405 | 40 | IV | 350 | 50 | III | 55 |
| 15 | 0.3 | 390 | 70 | IV | 360 | 70 | III | 30 |
| Comparison | 0.1 | 430 | 80 | IV | 385 | 80 | III | 45 |

[+] in % by weight of cobalt metal, based on polymer

The quantity of adhesive which is used in the rubber mixture corresponded to 0.3% by weight of cobalt metal, based on the polymer.

TABLE 3

| | Example 8 | Example 3 | Example 2 |
|---|---|---|---|
| Vulcanisation corresponding | | | |

TABLE 3-continued

|  | Example 8 | Example 3 | Example 2 |
|---|---|---|---|
| to the $t_{90}$ value of the mixture | | | |
| X (N/20 mm) | 380 | 380 | 380 |
| R (N/20 mm) | 80 | 30 | 45 |
| C | III | III | III |
| Additional ageing in a Geer furnace; duration: 6 days | | | |
| X (N/20 mm) | 360 | | |
| R (N/20 mm) | 55 | | |
| C | III | | |
| Additional ageing in superheated steam at 120° C. Duration: 4 days | | | |
| X (N/20 mm) | 275 | 320 | 320 |
| R (N/20 mm) | 60 | 20 | 60 |
| C | IV | III | IV |
| Additional ageing in humid atmosphere (95% RH) at 40° C. Duration: 1 month | | | |
| X (N/20 mm) | 330 | 300 | 310 |
| R (N/20 mm) | 60 | 70 | 80 |
| C | III | II | III |
| Vulcanisation at 180° C. for 45 min longer than corresponds to the $t_{90}$ value | | | |
| X (N/20 mm) | 280 | 280 | 280 |
| R (N/20 mm) | 25 | 75 | 30 |
| C | III | III | III |

The use of the adhesives according to the present invention is also advantageous in combination with adhesives of the "multicomponent system" type.

The resistance of the adhesion to thermal and humid stresses is also greatly improved. The test formulation stated below is used for the data given in the following. The other test conditions remain unchanged.

| Natural rubber (RSSI) | 100 parts by weight |
|---|---|
| Carbon black N-330 | 50 " |
| Highly active precipitated silica | 10 " |
| Phenol-formaldehyde resin | 4 " |
| Isopropyl-phenyl-p-phenylenediamine | 2.5 " |
| Zinc oxide | 6 " |
| Resorcinol | 2 " |
| Hexamethylolmelamine-pentamethylether (HMMM) | 2 " |
| Sulphur | 4.5 " |
| N,N—dicyclohexyl-thiobenzo-thiazole | 2 " |
| N—cyclohexyl-thiophthalimide | 0.3 " |
| Adhesive | as stated |

TABLE 4

| | Vulcanisation corresponding to the $t_{90}$ value of the mixture | | Additional ageing in superheated steam at 120° C. Duration: 2 days | |
|---|---|---|---|---|
| | Example 8 | Example 3 | Example 8 | Example 3 |
| Resorcinol + HMMM | | | | |
| $\bar{X}$ (N/20 mm) | 345 | | 170 | |
| R (N/20 mm) | 40 | | 30 | |
| C | IV | | GR | |
| Resorcinol + HMMM + adhesive of present invention | | | | |
| $\bar{X}$ (N/20 mm) | 365 | 370 | 295 | 225 |
| R (N/20 mm) | 70 | 68 | 35 | 40 |
| C | IV | IV | II | I |

We claim:

1. Compounds corresponding to the formula

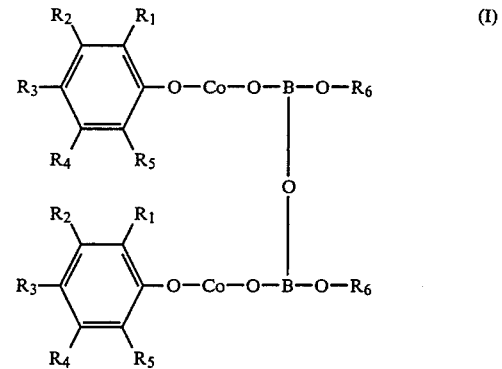

wherein $R_1$, $R_2$, $R_3$, $R_4$ and $R_5$ are the same or different, and represent hydrogen, hydroxy, $C_1$–$C_{18}$ alkyl, $C_5$–$C_{12}$ cycloalkyl, $C_1$–$C_{16}$ alkylthio, $C_6$–$C_{14}$ aryl, $C_6$–$C_{14}$ aryl-$C_1$–$C_4$ alkyl, $C_1$–$C_{18}$ alkoxy, $C_6$–$C_{14}$ aryloxy, $C_6$–$C_{14}$-aryl-$C_1$–$C_4$ alkyloxy, halogen or a hydrocarbon radical which has from 2 to 18 carbon atoms and has one or more double bonds, and $R_6$ represents a linear or branched, saturated or mono- or poly-unsaturated hydrocarbon radical having from 1 to 22 carbon atoms or a radical of the formula

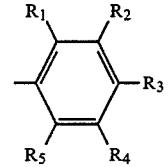

wherein $R_1$ to $R_5$ have the before-mentioned meaning.

2. Compounds according to claim 1, wherein $R_1$, $R_2$, $R_3$, $R_4$ and $R_5$ represent hydrogen, $C_6$–$C_{12}$ alkyl or $C_6$–$C_{14}$-aryl-$C_1$–$C_4$ alkyl, and $R_6$ represents a $C_8$–$C_{22}$ hydrocarbon radical.

* * * * *